United States Patent [19]

Dahlgren et al.

[11] Patent Number: 5,608,118
[45] Date of Patent: Mar. 4, 1997

[54] ALKOXYLATE OF 2-PROPYL HEPTANOL AND DETERGENT CONTAINING SAME

[75] Inventors: Lennart Dahlgren, Mjölnarvågen; Karin Bergström, Kungälv, both of Sweden

[73] Assignee: Berol Nobel AB

[21] Appl. No.: 436,268

[22] PCT Filed: Nov. 12, 1993

[86] PCT No.: PCT/SE93/00966

§ 371 Date: May 16, 1995

§ 102(e) Date: May 16, 1995

[87] PCT Pub. No.: WO94/11330

PCT Pub. Date: May 26, 1994

[30] Foreign Application Priority Data

Nov. 19, 1992 [SE] Sweden ............................. 9203478

[51] Int. Cl.$^6$ .................... C07C 43/11; C11D 1/72
[52] U.S. Cl. .......................................... 568/625
[58] Field of Search ................................ 568/625

[56] References Cited

U.S. PATENT DOCUMENTS 2,508,036 3/1950 Kosmin .
3,340,309 9/1967 Weipert et al. .
3,567,784 3/1971 Tsatsos et al. .
3,862,243 1/1975 Bellos .

FOREIGN PATENT DOCUMENTS 0046582 3/1982 European Pat. Off. .
2145726 4/1985 United Kingdom .
2194536 3/1988 United Kingdom .

*Primary Examiner*—Jeffrey C. Mullis
*Attorney, Agent, or Firm*—Spencer & Frank

[57] ABSTRACT

An alkoxylate of 2-propyl heptanol having from 1 to 6 alkyleneoxy groups (B) adducted to the oxygen of the alcohol and from 1 to 10 ethylene oxide group adducted to the terminal alkyleneoxy group and having a general formula (I)

$$C_5H_{11}CH(C_3H_7)CH_2O(B)_r(C_2H_4O)_pH \qquad (I),$$

wherein B is the alkyleneoxy group which has 3–4 carbon atoms, p is 1–10 and r is 1–6.

4 Claims, No Drawings

ALKOXYLATE OF 2-PROPYL HEPTANOL AND DETERGENT CONTAINING SAME

BACKGROUND OF THE INVENTION

1. Field of the Invention

The present invention relates to an alkoxylate of 2-propyl heptanol. The alkoxylate exhibits high detergent power on textile materials and low foaming compared with similar compounds having a hydrophobic group of approximately the same size and approximately the same HLB-value. The alkoxylate may advantageously be used as a surface-active component in detergent compositions for textile materials.

2. Description of the Related Art

It has long been known to alkoxylate alcohols for obtaining non-ionic surface-active compounds. These compounds have been used in detergent compositions because of their wetting and dispersing properties. In a number of applications, alkoxylates of $C_{8-11}$ alcohols have however been found to be too high-foaming and/or not to have the desired detergent power. For example, ethoxylates based on branched $C_8$ alcohols often exhibit acceptable foaming but too low a detergent power, whereas ethoxylates based on straight or branched alcohols having a larger hydrocarbon chain often show an acceptable surface activity but too high foaming. Thus, there is a need for new alkylene oxide adducts with an improved ratio of foaming to detergent power.

SUMMARY OF THE INVENTION

It has now been found that an alkoxylate based on 2-propyl heptanol has good detergent and wetting properties as well as low foaming as compared with other alcohols having substantially the same chain length. In addition, it has been found that the alkoxylate is easily degradable and has a surprisingly low biotoxicity. In tests, no skin-irritant effect has been noted.

The alkoxylate according to the invention can be illustrated by the formula $$C_5H_{11}CH(C_3H_7)CH_2O(B)_r(C_2H_4O)_pH \quad (I)$$

wherein B is an alkyleneoxy group having 3–4 carbon atoms, p is 1–10 and r is 1–6. Preferably, p is 2–8 and r is 1–4. In these compounds, the hydrophobic properties of the hydrocarbon chain have been enhanced by adding hydrophobic alkyleneoxy groups closest to the alcohol. The compounds have a good detergent power on textile materials while at the same time showing slightly lower foaming in relation to compounds having a hydrophobic group of approximately the same hydrophobicity and approximately the same HLB-value.

The alkoxylates according to the invention described above can be prepared by adding in a conventional manner in the presence of a conventional alkali catalyst, such as potassium hydroxide or sodium hydroxide, the above-mentioned amounts of alkylene oxide to 2-propyl heptanol, which is a so-called Guebert alcohol. According to a preferred mode of execution, the addition of ethylene oxide is performed using a conventional catalyst which gives a narrower distribution of added ethylene oxide than any alkali catalyst, such as NaOH or KOH. Thus prepared alkoxylates according to the invention have very low foaming. Examples of conventional catalysts giving a narrow distribution of added alkylene oxide are $Ca(OH)_2$, $Ba(OH)_2$, $Sr(OH)_2$ and hydrotalcite. The reaction is preferably conducted in the absence of free water to reduce the amount of by-products and usually at a temperature of 70°–180° C.

Textile-cleaning compositions including the alkoxylate according to the invention may also contain other surface-active compounds, such as anionic ones. Examples hereof are alkyl sulphate, alkyl ether sulphate, alkyl benzene sulphonate, α-olefin sulphonate and alkyl glyceryl sulphonate. Other commonly occurring components solubilizing additives, complexing agents and/or pH-adjusting agents, enzymes, bactericides and perfumes. The compositions are usually aqueous and in the form of emulsions, microemulsions or solutions.

DESCRIPTION OF THE PREFERRED EMBODIMENTS

The invention will be further illustrated by the following Examples.

EXAMPLE 1

An alkoxylate according to the invention are prepared by alkoxylating 2-propyl heptanol with the amounts of alkylene oxide appearing from the Table below in the presence of potassium hydroxide as catalyst. For reference purposes, two alkoxylates were prepared using a $C_{9-11}$ alcohol (Dobanol 91 Shell) as hydrophobic ingredient. The resulting products were analysed and structurally determined by gas chromatography and mass spectrometry. The turbidity points were measured in water or monobutylether diethylene glycol. The following results were obtained.

TABLE 1

| Compound | Alcohol | Mole of alkylene oxide/mole of alcohol | Catalyst | Turbidity point Water | Turbidity point BDG |
|---|---|---|---|---|---|
| 1 | 2-propyl heptanol | 4 PO + 6 EO[1] | KOH | 25 | — |
| A | $C_{9-11}$ alcohol | 4 EO | KOH | — | 62 |
| B | $C_{9-11}$ alcohol | 6 EO | KOH | 56 | — |

EO = ethylene oxide;
PO = propylene oxide,
BDG = monobutylether diethylene glycol
[1]PO added first

EXAMPLE 2

The foaming properties of the alkoxylates reported in the following Table were measured according to Ross-Miles ASTM D 1173–53. The following results were obtained.

TABLE 2

| Compound | Foam height, cm 0 min | Foam height, cm 5 min |
|---|---|---|
| 1 | 83 | 12 |
| A | 80 | 20 |
| B | 95 | 30 |

The compound according to the invention has equivalent or slightly lower foaming as compared with compounds A and B.

EXAMPLE 3

Washing tests were carried out in a Terg-0-Tometer on pigment-soiled cotton and cotton/polyester. Washed-away soil was thereafter determined by conventional reflectance measurement. The following results were obtained.

TABLE 3

| | Washed-away pigment soil, % | | |
|---|---|---|---|
| | Cotton | Cotton/polyester | |
| Compound | 40° C. | 40° C. | 60° C. |
| 1 | 78 | 73 | 66 |
| A | 78 | 65 | 52 |

From these results it appears that the compound according to the invention all in all has higher detergent power than the reference compound. From Example 2 also appears that the compound according to the invention has slightly lower foaming than the reference compound.

What is claimed is:

1. An alkoxylate of 2-propyl heptanol having from 1 to 6 alkyleneoxy groups (B) adducted to the oxygen of the alcohol and from 1 to 10 ethylene oxide groups adducted to the terminal alkyleneoxy group and having a general formula (I):

$$C_5H_{11}CH(C_3H_7)CH_2O(B)_r(C_2H_4O)_pH \quad (I),$$

wherein B is the alkyleneoxy group which has 3–4 carbon atoms, p is 1–10 and r is 1–6.

2. The alkoxylate as claimed in claim 1, wherein p is 2–8 and r is 1–4.

3. A detergent composition for textile materials, comprising an alkoxylate of 2-propyl heptanol as defined in claim 1.

4. A detergent composition for textile materials, comprising an alkoxylate of 2-propyl heptanol as defined in claim 2.

* * * * *